US008840733B2

(12) United States Patent
Komiya et al.

(10) Patent No.: US 8,840,733 B2
(45) Date of Patent: Sep. 23, 2014

(54) ENDOSCOPE CLEANING/DISINFECTING APPARATUS

(71) Applicant: Olympus Medical Systems Corp., Tokyo (JP)

(72) Inventors: Jiro Komiya, Hachioji (JP); Norito Sato, Hachioji (JP); Hisashi Kuroshima, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 13/741,744

(22) Filed: Jan. 15, 2013

(65) Prior Publication Data

US 2013/0125934 A1 May 23, 2013

Related U.S. Application Data

(63) Continuation of application No. PCT/JP2012/059793, filed on Apr. 10, 2012.

(30) Foreign Application Priority Data

Jul. 15, 2011 (JP) ................................. 2011-156989

(51) Int. Cl.
*B08B 9/027* (2006.01)
*A61B 1/12* (2006.01)
*A61L 2/28* (2006.01)
*A61L 2/18* (2006.01)

(52) U.S. Cl.
CPC ................. *B08B 9/027* (2013.01); *A61B 1/125* (2013.01); *A61L 2202/24* (2013.01); *A61B 1/123* (2013.01); *A61L 2/28* (2013.01); *A61L 2/18* (2013.01)
USPC ............... 134/166 C; 134/167 C; 134/168 C; 134/169 C

(58) Field of Classification Search
CPC ........ A61B 1/123; A61B 1/125; B08B 9/027; A61L 2/18; A61L 2204/24; A61L 2/28
USPC ................... 134/166 C, 167 C, 168 C, 169 C
See application file for complete search history.

(56) References Cited

U.S. PATENT DOCUMENTS

2005/0000553 A1* 1/2005 Noguchi et al. ................. 134/84
2005/0209507 A1 9/2005 Suzuki et al.
(Continued)

FOREIGN PATENT DOCUMENTS

JP 5-43763 11/1993
JP 09-028669 2/1997
(Continued)

OTHER PUBLICATIONS

Extended Supplementary European Search Report dated Jan. 14, 2014 from related European Application No. 12 81 5415.0.

*Primary Examiner* — Michael Barr
*Assistant Examiner* — Benjamin Osterhout
(74) *Attorney, Agent, or Firm* — Scully, Scott, Murphy & Presser, P.C.

(57) ABSTRACT

An endoscope cleaning/disinfecting apparatus includes: a medicinal solution storage portion; a cleaning/disinfecting tank; a medicinal solution supplying conduit having one end communicating with the medicinal solution storage portion and the other end opening toward the cleaning/disinfecting tank; a medicinal solution supplying member; a medicinal solution receiving member provided inside the medicinal solution supplying member; and a medicinal solution collecting port which is openable/closable by a lid body, and formed at a position between the medicinal solution receiving member and the opening of the other end in the medicinal solution supplying conduit.

6 Claims, 9 Drawing Sheets

(56) References Cited

U.S. PATENT DOCUMENTS

2007/0107755 A1* 5/2007 Noguchi et al. ............. 134/94.1
2008/0295277 A1* 12/2008 Onishii ........................ 15/302
2009/0044845 A1* 2/2009 Cui et al. ..................... 134/56 R
2009/0081767 A1 3/2009 Ogawa et al.
2010/0252074 A1* 10/2010 Sewake et al. ................. 134/19

FOREIGN PATENT DOCUMENTS

| | | |
|---|---|---|
| JP | 2003-038438 | 2/2003 |
| JP | 2010-051574 | 3/2010 |
| JP | 2011-092425 | 5/2011 |

* cited by examiner

US 8,840,733 B2

ENDOSCOPE CLEANING/DISINFECTING APPARATUS

CROSS REFERENCE TO RELATED APPLICATION

This application is a continuation application of PCT/JP2012/059793 filed on Apr. 10, 2012 and claims benefit of Japanese Application No. 2011-156989 filed in Japan on Jul. 15, 2011, the entire contents of which are incorporated herein by this reference.

BACKGROUND OF THE INVENTION

1. Field of the Invention

The present invention relates to an endoscope cleaning/disinfecting apparatus which supplies a medicinal solution to a cleaning/disinfecting tank from a medicinal solution storage portion through a medicinal solution supplying conduit by driving of a medicinal solution supplying member.

2. Description of the Related Art

Medicinal solution processing of an endoscope using an endoscope cleaning/disinfecting apparatus is performed by supplying a medicinal solution from a medicinal solution storage portion to a cleaning/disinfecting tank in which the endoscope is housed, through a medicinal solution supplying conduit.

In addition, since a concentration control of the medicinal solution is important in order to unfailingly perform the medicinal solution processing of the endoscope, it is common that concentration check of the medicinal solution is performed for each process in the medicinal solution processing.

Japanese Patent Application Laid-Open Publication No. 2010-51574 discloses an endoscope cleaning/disinfecting apparatus including a medicinal solution storage portion provided at a lower position than a cleaning/disinfecting tank, wherein concentration check of medicinal solution is performed by extracting a specified amount of medicinal solution from a medicinal solution extraction hole of a medicinal solution storage portion, to dip a test paper in the extracted medicinal solution and observe a change in color of the test paper, or to quantify the concentration of the extracted medicinal solution using a concentration measuring apparatus.

In addition, the endoscope cleaning/disinfecting apparatus can be configured such that the medicinal solution storage portion is provided at an upper side of the endoscope cleaning/disinfecting apparatus.

Furthermore, it is possible to conceive a method of removing an odor filter provided to a top cover which seals the cleaning/disinfecting tank of the endoscope cleaning/disinfecting apparatus, to extract the medicinal solution through the opening for the odor filter, or directly insert the test paper in the cleaning/disinfecting tank, during the cleaning/disinfecting processing.

SUMMARY OF THE INVENTION

An endoscope cleaning/disinfecting apparatus according to one aspect of the present invention comprises: a medicinal solution storage portion configured to store a medicinal solution; a cleaning/disinfecting tank in which an endoscope is cleaned and disinfected, the cleaning/disinfecting tank being arranged at a higher position than the medicinal solution storage portion; a medicinal solution supplying conduit configured to allow the medicinal solution to pass from the medicinal solution storage portion to the cleaning/disinfecting tank, the medicinal solution supplying conduit having one end communicating with the medicinal solution storage portion and the other end opening toward the cleaning/disinfecting tank; a medicinal solution supplying member configured to be driven so as to feed the medicinal solution in a gravity-defying flow direction from the medicinal solution storage portion to the cleaning/disinfecting tank through the medicinal solution supplying conduit; a medicinal solution receiving member provided inside the medicinal solution supplying conduit; and a medicinal solution collecting port configured to be openable/closable by a lid body, and provided at a position between the medicinal solution receiving member and the opening of the other end in the medicinal solution supplying conduit, wherein the medicinal solution receiving member is a check valve configured to allow the medicinal solution flowing from the medicinal solution storage portion to the cleaning/disinfecting tank to pass and configured to receive a part of the medicinal solution fed from the medicinal solution storage portion to the cleaning/disinfecting tank, the part of the medicinal solution being fallen down by gravity without being supplied from the opening of the other end to the cleaning/disinfecting tank due to a stop of driving of the medicinal solution supplying member.

DETAILED DESCRIPTION OF THE PREFERRED EMBODIMENT(S)

Hereinafter, an embodiment of the present invention is described with reference to drawings. Note that each of the drawings is a pattern diagram, and care should be taken to the fact that the relationship between the thicknesses and widths of the respective members, a ratio of the thickness of a certain member to that of another member, and the like are different from the actual sizes. It is needless to say that each of the drawings includes a different relationship and ratio among the dimensions.

Figure 1:
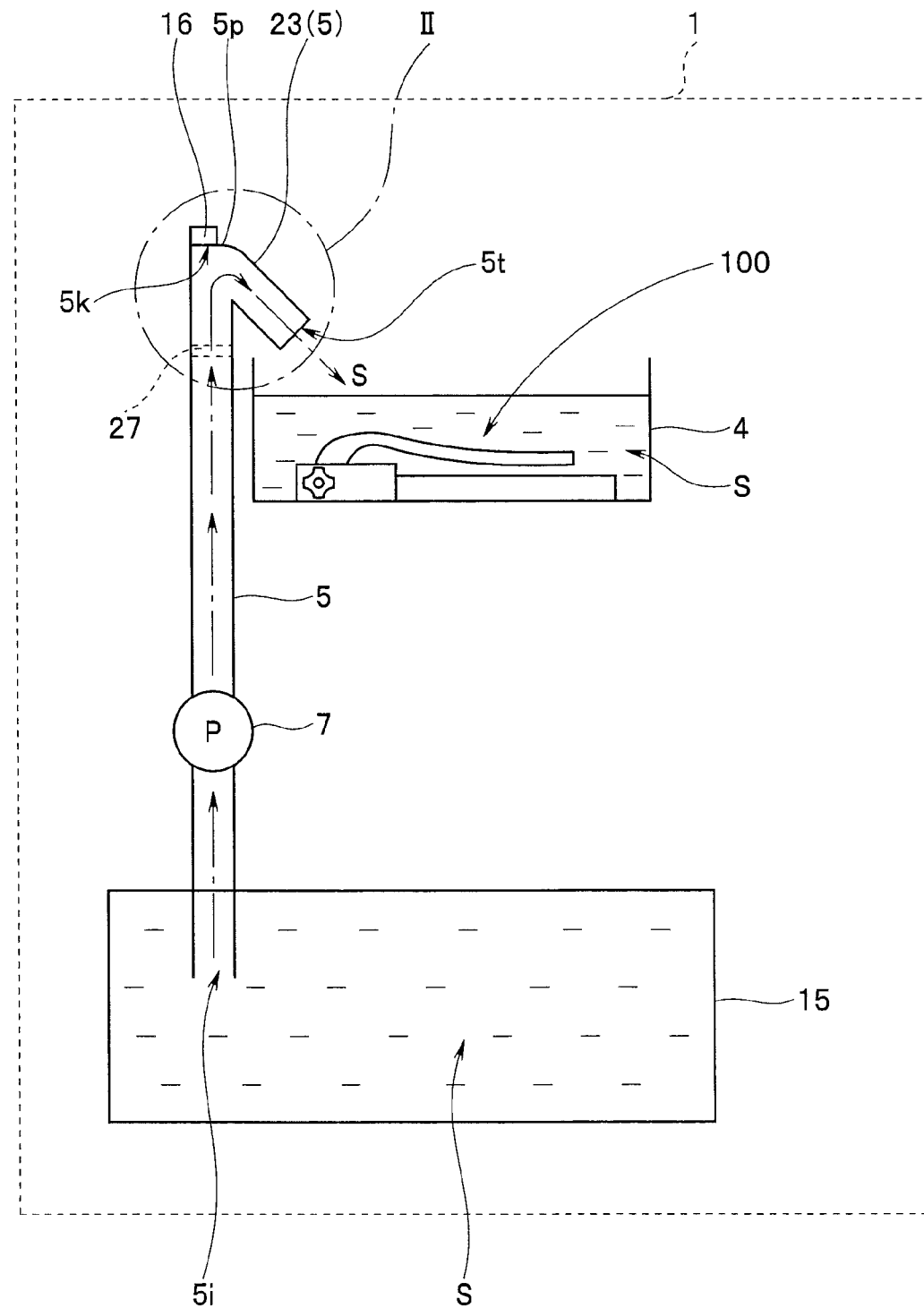
FIG. 1 illustrates a simple overview of a configuration of a main part of an endoscope cleaning/disinfecting apparatus according to a present embodiment.
Figure 2:
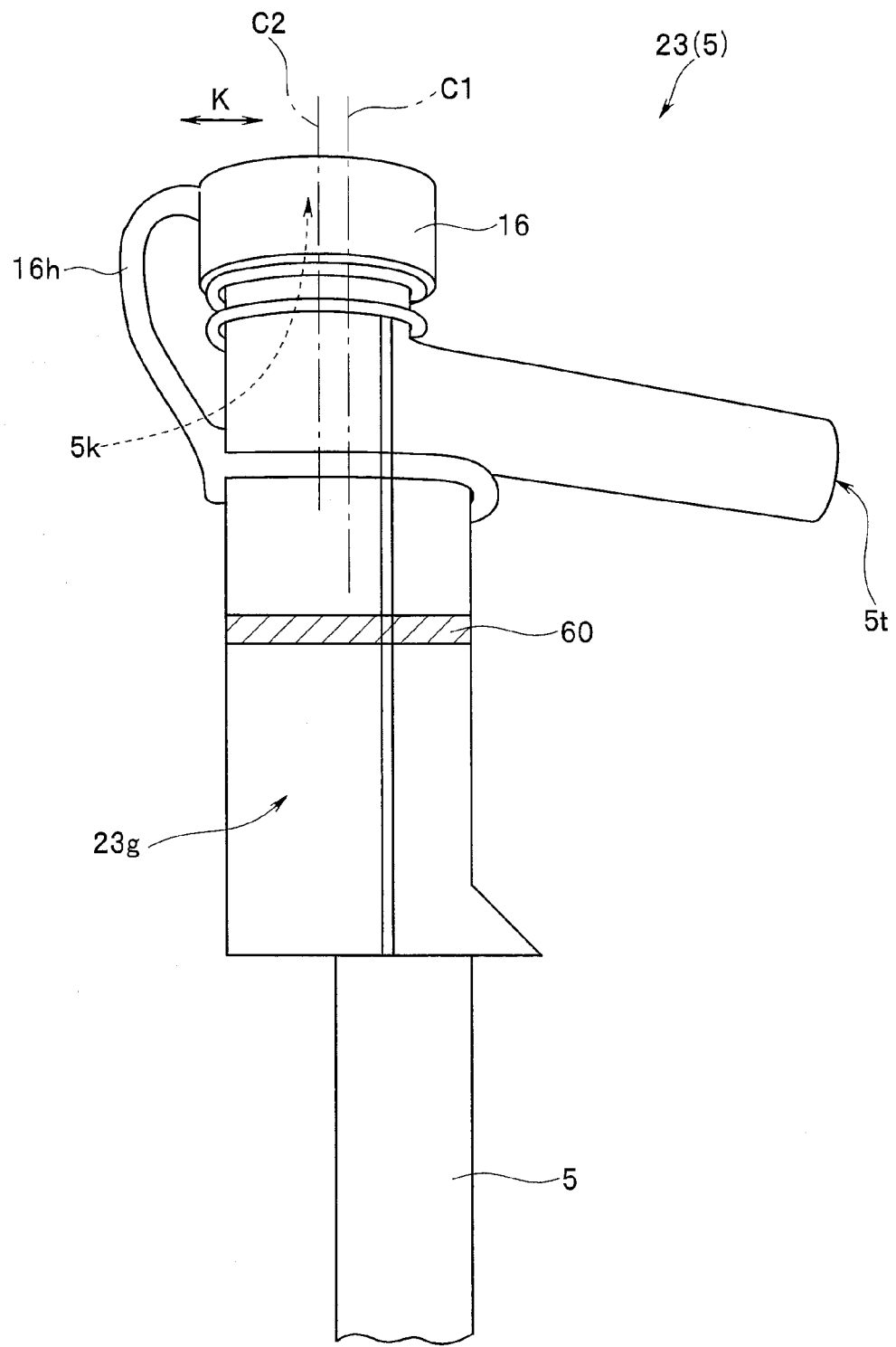
FIG. 2 is a front view of a medicinal solution supplying nozzle in the part enclosed by the line II in FIG. 1.
Figure 3:
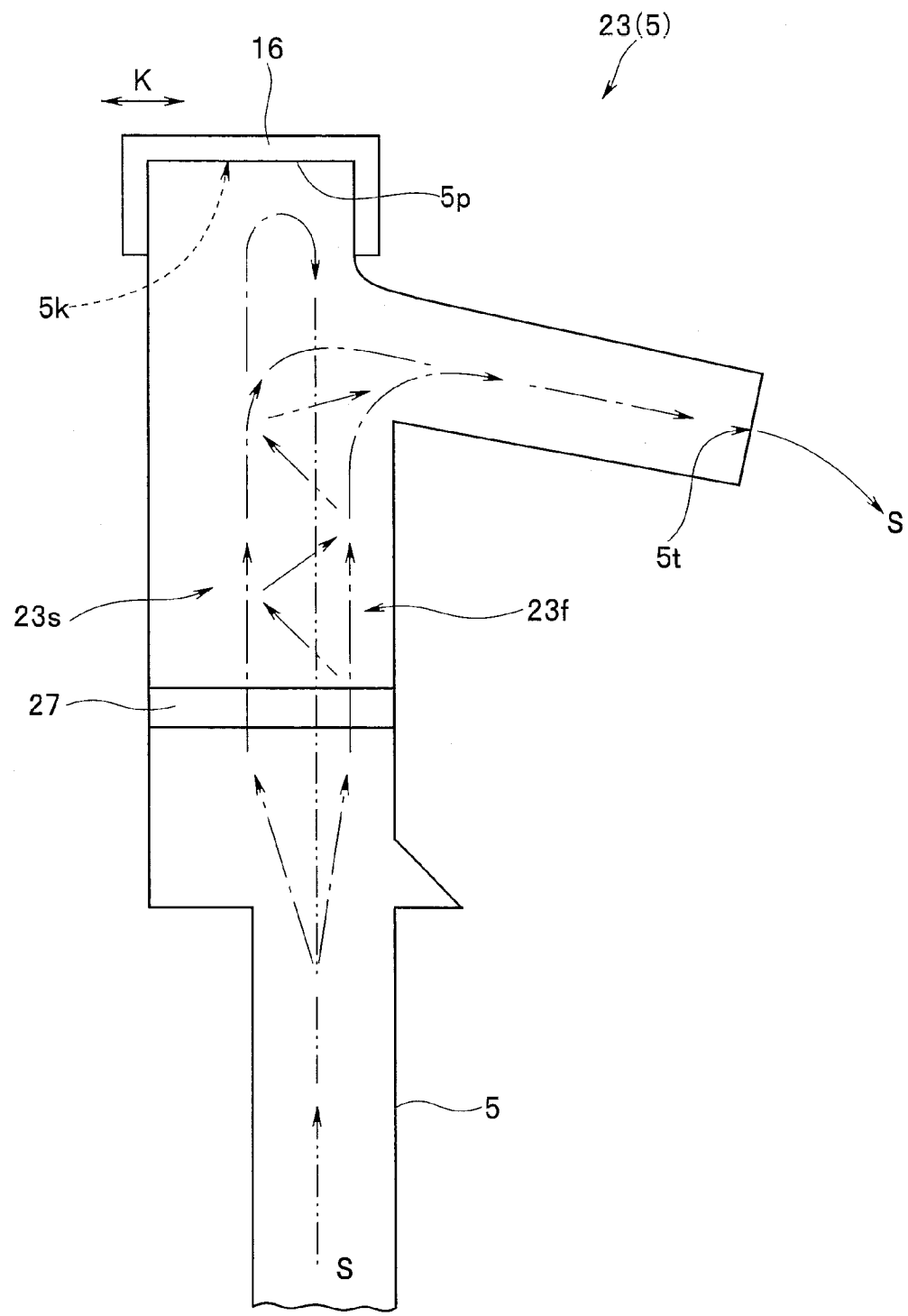
FIG. 3 illustrates an internal configuration of the medicinal solution supplying nozzle in FIG. 2.

FIG. 1 illustrates a simple overview of a configuration of a main part of an endoscope cleaning/disinfecting apparatus according to the present embodiment. FIG. 2 is a front view of a medicinal solution supplying nozzle in the part enclosed by the line II in FIG. 1. FIG. 3 illustrates an internal configuration of the medicinal solution supplying nozzle in FIG. 2.

Figure 4:
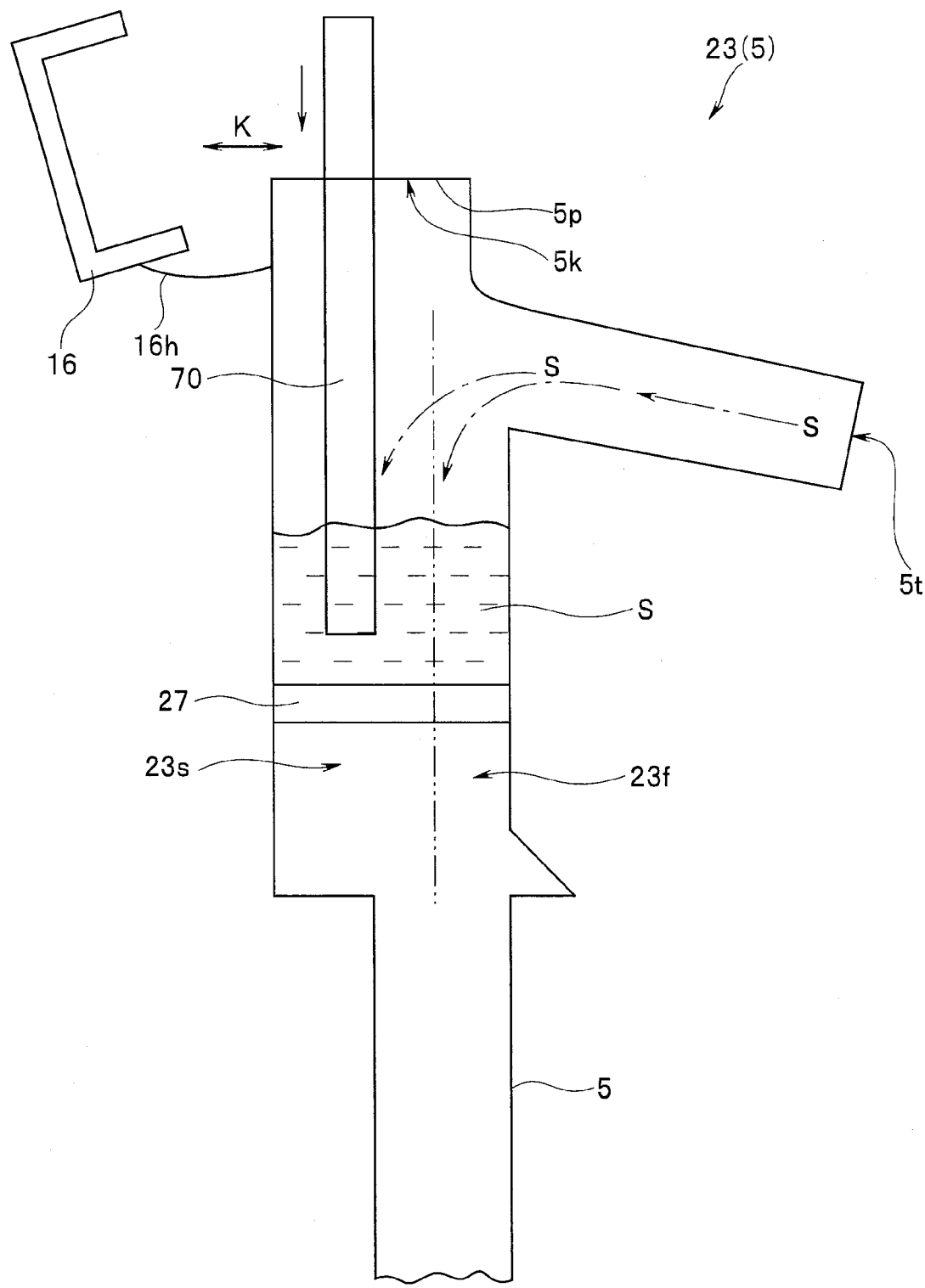
FIG. 4 schematically illustrates a state in which a test paper is inserted from a medicinal solution collecting port of the medicinal solution supplying nozzle in FIG. 1.
Figure 5:
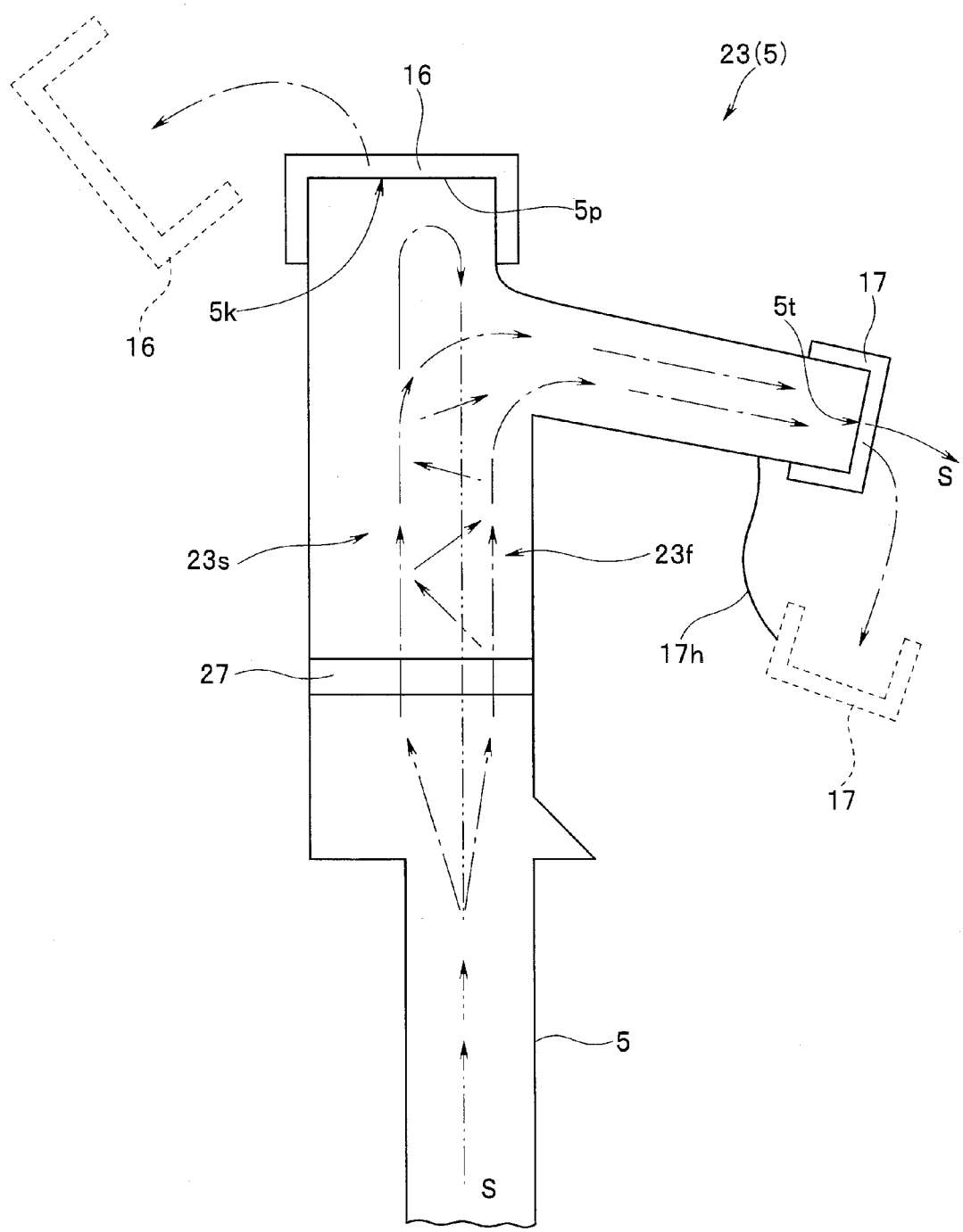
FIG. 5 illustrates the medicinal solution supplying nozzle configured such that lid bodies are attachable to and detachable from an opening at the other end of a medicinal solution supplying conduit and the medicinal solution collecting port in FIG. 1, respectively.
Figure 6:
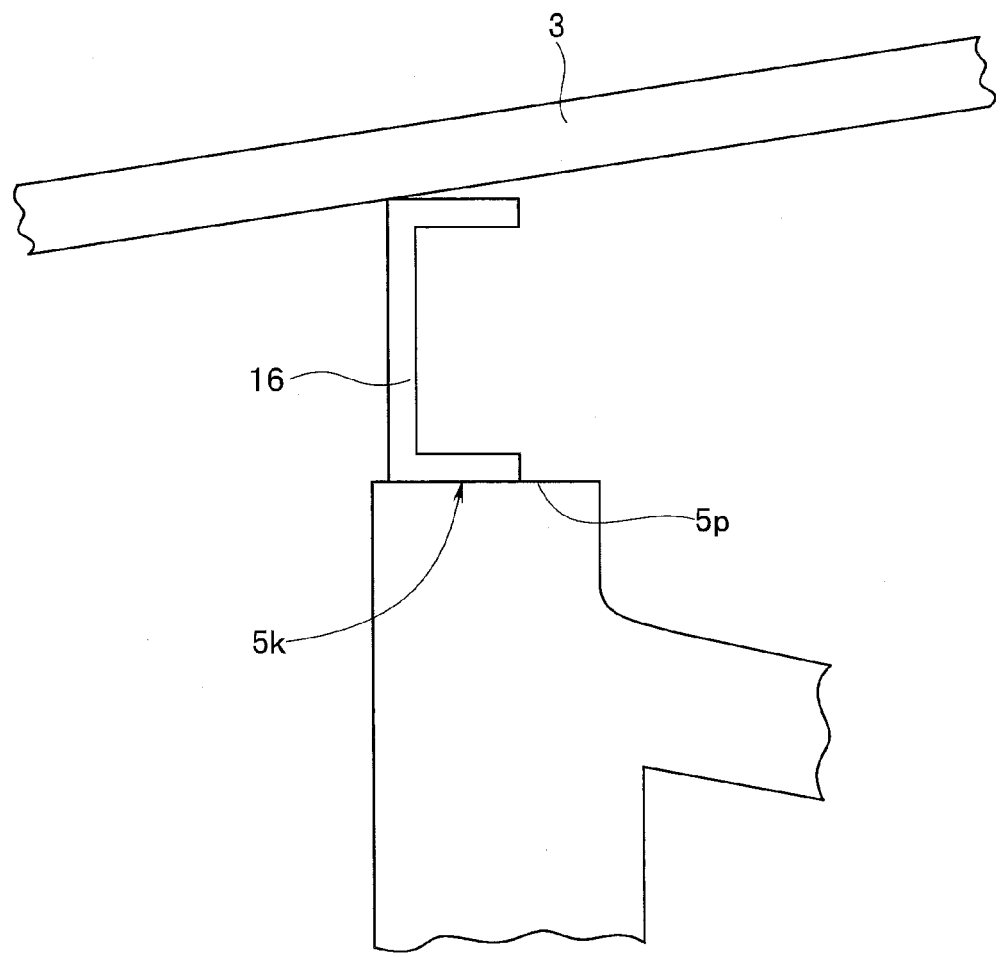
FIG. 6 illustrates a state where a top cover of the endoscope cleaning/disinfecting apparatus contacts the lid body when the lid body is placed on the medicinal solution collecting port in FIG. 1.

Furthermore, FIG. 4 schematically illustrates a state in which a test paper is inserted from a medicinal solution collecting port of the medicinal solution supplying nozzle in FIG. 1. FIG. 5 illustrates the medicinal solution supplying nozzle configured such that lid bodies are attachable to and detachable from an opening at the other end of a medicinal solution supplying conduit and the medicinal solution collecting port in FIG. 1, respectively. FIG. 6 illustrates a state where a top cover of the endoscope cleaning/disinfecting apparatus contacts the lid body when the lid body is placed on the medicinal solution collecting port in FIG. 1.

As shown in FIG. 1, an endoscope cleaning/disinfecting apparatus 1 includes a medicinal solution storage portion 15 in which medicinal solution S is stored, and also includes, at a higher position than the medicinal solution storage portion 15, a cleaning/disinfecting tank 4 in which an endoscope 100 is cleaned and disinfected. Note that a disinfectant solution can be named as the medicinal solution S, for example, however, the medicinal solution is not limited to the disinfectant solution.

In addition, the medicinal solution storage portion 15 and the cleaning/disinfecting tank 4 are connected with each other by a medicinal solution supplying conduit 5. Specifically, one end 5*i* of the medicinal solution supplying conduit 5 is communicated with the medicinal solution storage portion 15 in the medicinal solution storage portion 15 and the other end 5*t* is open toward the cleaning/disinfecting tank 4, for example, thereby causing the medicinal solution S stored in the medicinal solution storage portion 15 to flow into the medicinal solution supplying conduit 5 from the one end 5*i*, pass through the medicinal solution supplying conduit 5, to be supplied to the cleaning/disinfecting tank 4 from the other end 5*t*.

As shown in FIG. 5, a lid body 17, which prevents odor of the medicinal solution S in the medicinal solution supplying conduit 5 from leaking outside the endoscope cleaning/disinfecting apparatus 1, is attachable to and detachable from the opening of the other end 5*t*.

In addition, the lid body 17 is detached when the medicinal solution S is supplied from the medicinal solution storage portion 15 to the cleaning/disinfecting tank 4 through the medicinal solution supplying conduit 5. Furthermore, the lid body 17 is connected to the other end side of the medicinal solution supplying conduit 5 through a string 17*h* and the like so as not to be lost after the lid body is detached.

Furthermore, the lid body 17 is configured so as to be detached with lower pressure of the medicinal solution S, compared with the lid body 16 to be described later. This is because, even in a case where a worker forgets to detach the lid body 17, if the lid body can be detached with lower pressure, the lid body 17 can be automatically detached by supplying the medicinal solution S from the medicinal solution storage portion 15.

A medicinal solution supplying member 7 which is driven such that the medicinal solution S is fed from the medicinal solution storage portion 15 to the cleaning/disinfecting tank 4 through the medicinal solution supplying conduit 5 is arranged in the medicinal solution supplying conduit 5, for example. Note that a fluid supplying pump and the like can be named as the medicinal solution supplying member 7. However, the medicinal solution supplying member is not limited to a pump, but may be a member configured to push out the medicinal solution S by contracting the medicinal solution storage portion 15 or may be a member configured to pressurize the inside of the medicinal solution storage portion 15. In such a case, the arranging position of the medicinal solution supplying member 7 is adjacent to the position of the medicinal solution storage portion 15.

At least a part of the other end side including the opening of the other end 5*t* of the medicinal solution supplying conduit 5 is arranged at a position higher than the cleaning/disinfecting tank 4, and is formed to be partly bent such that the other end 5*t* opens toward the cleaning/disinfecting tank 4. The bent part of the other end side of the medicinal solution supplying conduit 5 configures a medicinal solution supplying nozzle 23. That is, the medicinal solution supplying nozzle 23 configures a part of the medicinal solution supplying conduit 5.

A medicinal solution receiving member 27 is provided in the medicinal solution supplying conduit 5. When a pump is used as the medicinal solution supplying member 7, the medicinal solution supplying member 7 is provided in the medicinal solution supplying conduit 5 at a position closer to the side of the opening of the other end 5*t* than the medicinal solution supplying member 7, more specifically, the medicinal solution receiving portion 27 is provided in a medicinal solution supplying nozzle 23 as shown in FIG. 3.

The medicinal solution receiving member 27 is configured to receive a part of the medicinal solution S which is fed from the medicinal solution storage portion 15 to the cleaning/disinfecting tank 4 with the driving of the medicinal solution supplying member 7, that is, the part of the medicinal solution S falling toward the medicinal solution storage position 15 by gravity, without being supplied from the opening of the other end St to the cleaning/disinfecting tank 4 due to a stop of driving of the medicinal solution supplying member 7, and configured to store a predetermined amount of medicinal solution S in the medicinal solution supplying nozzle 23.

Note that, in the present embodiment, as the medicinal solution receiving member 27, a valve portion which prevents the medicinal solution from flowing backward by gravity to one end 5*i* from the other end 5*t* in the medicinal solution supplying conduit 5, more specifically, a check valve or an electromagnetic valve can be named. However, since the electromagnetic valve requires open/close control, the check valve is more preferable.

In addition, when the medicinal solution receiving member 27 is configured by the electromagnetic valve, closing of the electromagnetic valve has to be performed after a certain time period has passed after the stop of driving of the medicinal solution supplying member 7. This is because, when the medicinal solution supplying member 7 is configured by a pump, the pump does not stop immediately even if the stop switch of the pump is depressed, and if the electromagnetic valve is closed immediately after the depression of the stop switch of the pump, there is a possibility that the pump is broken.

In addition, a medicinal solution collecting port 5*k*, which allows inside of the medicinal solution supplying nozzle 23 to communicate with outside, is provided in the medicinal solution supplying conduit 5 at a position between the medicinal solution receiving member 27 and the opening of the other end 5*t* as shown in FIGS. 3 to 5, more specifically, provided in the medicinal solution supplying nozzle 23 so as to be located at a top portion 5*p* positioned higher than the opening of the other end 5*t*, as shown in FIGS. 1 to 6.

Note that the medicinal solution collecting port 5k is openable/closable by the lid body 16 which prevents the odor of the medicinal solution S in the medicinal solution supplying conduit 5 from leaking outside the endoscope cleaning/disinfecting apparatus 1. In addition, the lid body 16 is connected to the medicinal solution supplying nozzle 23 with a string 16h and the like so as not to be lost after the lid body is detached, as shown in FIGS. 2 and 4.

Furthermore, if the lid body 16, after having been detached from the medicinal solution collecting port 5k, is placed on the medicinal solution collecting port 5k as shown in FIG. 6, when a top cover 3, to be described later, which seals the cleaning/disinfecting tank 4 of the endoscope cleaning/disinfecting apparatus 1 contacts the lid body 16, the top cover 3 cannot be closed, thereby capable of reminding the worker of failure of attachment of the lid body 16.

In addition, as shown in FIG. 2, at the top portion 5p of the medicinal solution supplying nozzle 23, the medicinal solution collecting port 5k is arranged such that a center C2 of the medicinal solution collecting port 5k is positioned eccentrically toward a side further away from the other end 5t in a diameter direction K of the medicinal solution supplying conduit 5 than a conduit center C1 in a region from the medicinal solution collecting port 5k to the medicinal solution receiving member 27 of the medicinal solution supplying nozzle 23.

This is because, if the center C2 of the medicinal solution collecting port 5k coincides with the conduit center C1, when the worker forgets to attach the lid body 16 to the medicinal solution collecting port 5k, there is a possibility that the medicinal solution S will be spouted out from the medicinal solution collecting port 5k while the medicinal solution S is supplied from the medicinal solution storage portion 15 to the cleaning/disinfecting tank 4 through the medicinal solution supplying conduit 5, or even if the lid body 16 is attached to the medicinal solution collecting port 5k, the lid body 16 will be detached due to water pressure.

The medicinal solution collecting port 5k is an opening through which a test paper 70 is passed, when the test paper 70 such as a test strip is introduced into the inside of the medicinal solution supplying nozzle 23 to dip the distal end side of the test paper 70 in the medicinal solution S stored in the medicinal solution supplying nozzle 23 by the medicinal solution receiving member 27.

Note that the medicinal solution collecting port 5k is not limited to the opening for the test paper 70, but may be an opening through which a pipette or the like for collecting the medicinal solution S directly from inside of the medicinal solution supplying nozzle 23 passes.

In addition, inside the medicinal solution supplying nozzle 23, it is preferable that the region from the medicinal solution collecting port 5k to the medicinal solution receiving member 27 has a linear shape.

This is because, if the region from the medicinal solution collecting port 5k to the medicinal solution receiving member 27 has a linear shape, when the medicinal solution S stored in the medicinal solution supplying nozzle 23 by the medicinal solution receiving member 27 is directly collected using the pipette or the like through the medicinal solution collecting port 5k, the pipette or the like is inserted into the medicinal solution collecting port 5k and thereafter only has to be advanced straight, which enables the distal end of the pipette to easily reach the medicinal solution S. That is, it is possible to collect the medicinal solution S using an existing collecting instrument without using a special collecting instrument.

In addition, as shown in FIGS. 3 to 5, inside the medicinal solution supplying nozzle 23, in the region from the medicinal solution collecting port 5k to the medicinal solution receiving member 27, a first flow passage 23f which configures a part of a flow passage through which the medicinal solution S passes from the one end 5i to the other end 5t of the medicinal solution supplying conduit 5 and a second flow passage 23s which communicates with the first flow passage 23f and linearly connects the medicinal solution collecting port 5k and the medicinal solution receiving member 27 are formed.

Note that the second flow passage 23s is a flow passage through which the test paper 70 or a collecting instrument such as a pipette inserted from the medicinal solution collecting port 5k passes. Accordingly, the medicinal solution S stored inside the medicinal solution supplying nozzle 23 by the medicinal solution receiving member 27 is enough to be stored at least in the second flow passage 23s.

Furthermore, since the second flow passage 23s communicates with the first flow passage 23f, when the medicinal solution S is supplied from the one end 5i to the other end 5t of the medicinal solution supplying conduit 5, the medicinal solution S constantly circulates between the first flow passage 23f and the second flow passage 23s, as shown in FIGS. 3 and 5, thereby preventing old medicinal solution S from remaining in the second flow passage 23s. That is, new medicinal solution S is always stored in the second flow passage 23s.

In addition, similarly as the medicinal solution collecting port 5k, the second flow passage 23s is arranged such that the center thereof is positioned eccentrically toward the side further away from the other end 5t than the conduit center C1 in the diameter direction K.

Since the second flow passage 23s is eccentric and the two flow passages 23f and 23s are provided inside the medicinal solution supplying nozzle 23, even if the worker forgets to attach the lid body 16 to the medicinal solution collecting port 5k, the medicinal solution S is prevented from spouting out from the medicinal solution collecting port 5k during the supply of the medicinal solution S from the medicinal solution storage portion 15 to the cleaning/disinfecting tank 4 through the medicinal solution supplying conduit 5. Furthermore, even if the lid body 16 is attached to the medicinal solution collecting port 5k, the lid body 16 is prevented from being detached due to water pressure.

This is because the flow amount and water pressure of the medicinal solution S supplied from the one end 5i are dispersed in the two flow passages 23f and 23s in the medicinal solution supplying nozzle 23.

Note that, when the second flow passage 23s is positioned so as to be greatly eccentric from the first flow passage 23f in the diameter direction K, even if the second flow passage 23s communicates with the first flow passage 23f, it is difficult to replace the medicinal solution S with new medicinal solution, and as a result, old medicinal solution S is more likely to remain. Therefore, it is preferable that the amount of eccentricity of the second flow passage 23s is set to an extent capable of preventing the old medicinal solution S from remaining and preventing the medicinal solution S from spouting out from the medicinal solution collecting port 5k.

In addition, as shown in FIG. 2, an indicator 60 for notifying the liquid surface level of the medicinal solution S stored in the medicinal solution supplying nozzle 23 by the medicinal solution receiving member 27 may be formed on the exterior portion of the medicinal solution supplying nozzle 23 so as to be located in the region from the medicinal solution collecting port 5k to the medicinal solution receiving member 27.

If the indicator 60 is formed on the medicinal solution supplying nozzle 23, when the test paper 70 or the collecting instrument such as a pipette are inserted into the medicinal solution supplying nozzle 23 from the medicinal solution collecting port 5$k$, even if the exterior portion of the medicinal solution supplying nozzle 23 is formed by a colored member and inside of the medicinal solution supplying nozzle 23 cannot be seen, the indicator enables the worker to easily recognize how far the test paper or the like should be inserted to reach the medicinal solution S.

Note that, instead of providing the indicator 60, also in a case where the medicinal solution supplying nozzle 23 is made of a transparent member, the same effect as that of the indicator 60 can be achieved. Note that, since other configurations of the endoscope cleaning/disinfecting apparatus 1 are the same as those in conventional apparatuses, the description thereof will be omitted.

Next, description will be made on the working of the present embodiment, more specifically, on a method of checking the concentration of the medicinal solution S.

As shown in FIG. 1, the worker first drives the medicinal solution supplying member 7 to cause the medicinal solution S to be supplied from the medicinal solution storage portion 15 through the medicinal solution supplying conduit 5 to the cleaning/disinfecting tank 4 from the opening of the other end 5$t$.

Then, after supplying a predetermined amount of the medicinal solution S to the cleaning/disinfecting tank 4, the worker stops driving of the medicinal solution supplying member 7. As a result, with the stop of driving of the medicinal solution supplying member 7, the medicinal solution S in the medicinal solution supplying conduit 5 which was not supplied to the cleaning/disinfecting tank 4 from the opening of the other end S$t$ falls down by gravity toward the one end 5$i$ of the medicinal solution supplying conduit 5. However, the fallen medicinal solution S is received by the medicinal solution receiving member 27 in the medicinal solution supplying nozzle 23 to be stored in the medicinal solution supplying nozzle 23.

Next, the worker removes the lid body 16 from the medicinal solution collecting port 5$k$, inserts the test paper 70 in the medicinal solution supplying nozzle 23 through the medicinal solution collecting port 5$k$, and dip the distal end side of the test paper 70 in the medicinal solution S stored by the medicinal solution receiving member 27, as shown in FIG. 4.

Finally, the worker extracts the test paper 70 through the medicinal solution collecting port 5$k$ and attaches the lid body 16 to the medicinal solution collecting port 5$k$, to determine the concentration of the medicinal solution S based on the color of the part dipped in the medicinal solution S of the extracted test paper 70.

Note that, needless to say, without using the test paper 70, a collecting instrument such as a pipette may be inserted into the medicinal solution supplying nozzle 23 through the medicinal solution collecting port 5$k$ to collect the medicinal solution S stored by the medicinal solution receiving member 27, and the collecting instrument may be extracted through the medicinal solution collecting port 5$k$ to measure the concentration of the collected medicinal solution S using a measuring apparatus.

Thus, in the present embodiment, the medicinal solution supplying nozzle 23 includes inside thereof the medicinal solution receiving member 27 for receiving the medicinal solution S fallen by gravity toward the one end 5$i$ after the driving of the medicinal solution supplying member 7 is stopped, and the medicinal solution supplying nozzle 23 includes, at the top portion 5$p$, the medicinal solution collecting port 5$k$ through which the test paper 70 or the collecting instrument is inserted into the medicinal solution supplying nozzle 23.

According to such a configuration, the test paper 70 or the collecting instrument is inserted into the medicinal solution supplying nozzle 23 through the medicinal solution collecting port 5$k$, and it is possible to easily check the concentration of the medicinal solution S only by dipping the test paper 70 into the medicinal solution S received by the medicinal solution receiving member 27 or by collecting the medicinal solution S using the collecting instrument.

Therefore, the medicinal solution S can be collected and the concentration of the medicinal solution S can be measured with a simple configuration in which only the medicinal solution receiving member 27 is provided in the existing medicinal solution supplying nozzle 23 and the medicinal solution collecting port 5$k$ is provided at the top portion 5$p$.

Therefore, there is no need for separately providing a conduit for collecting the medicinal solution S, and in addition, there is no need for waiting until the medicinal solution S is fully stored in the cleaning/disinfecting tank 4. Accordingly, after cleaning and disinfecting the endoscope 100, the worker can check the concentration of the medicinal solution S through the medicinal solution collecting port 5$k$ at any time, which provides an excellent workability.

Furthermore, the medicinal solution collecting port 5$k$ is formed at the top portion 5$p$ of the medicinal solution supplying nozzle 23. Accordingly, when checking the concentration of the medicinal solution S, the worker can perform the operation from the upper part of the endoscope cleaning/disinfecting apparatus 1, and it is not necessary for the worker to crouch down.

As described above, it is possible to provide easily and at low cost the endoscope cleaning/disinfecting apparatus 1 having a configuration which enables the concentration of the medicinal solution S to be checked with excellent workability.

Figure 7:
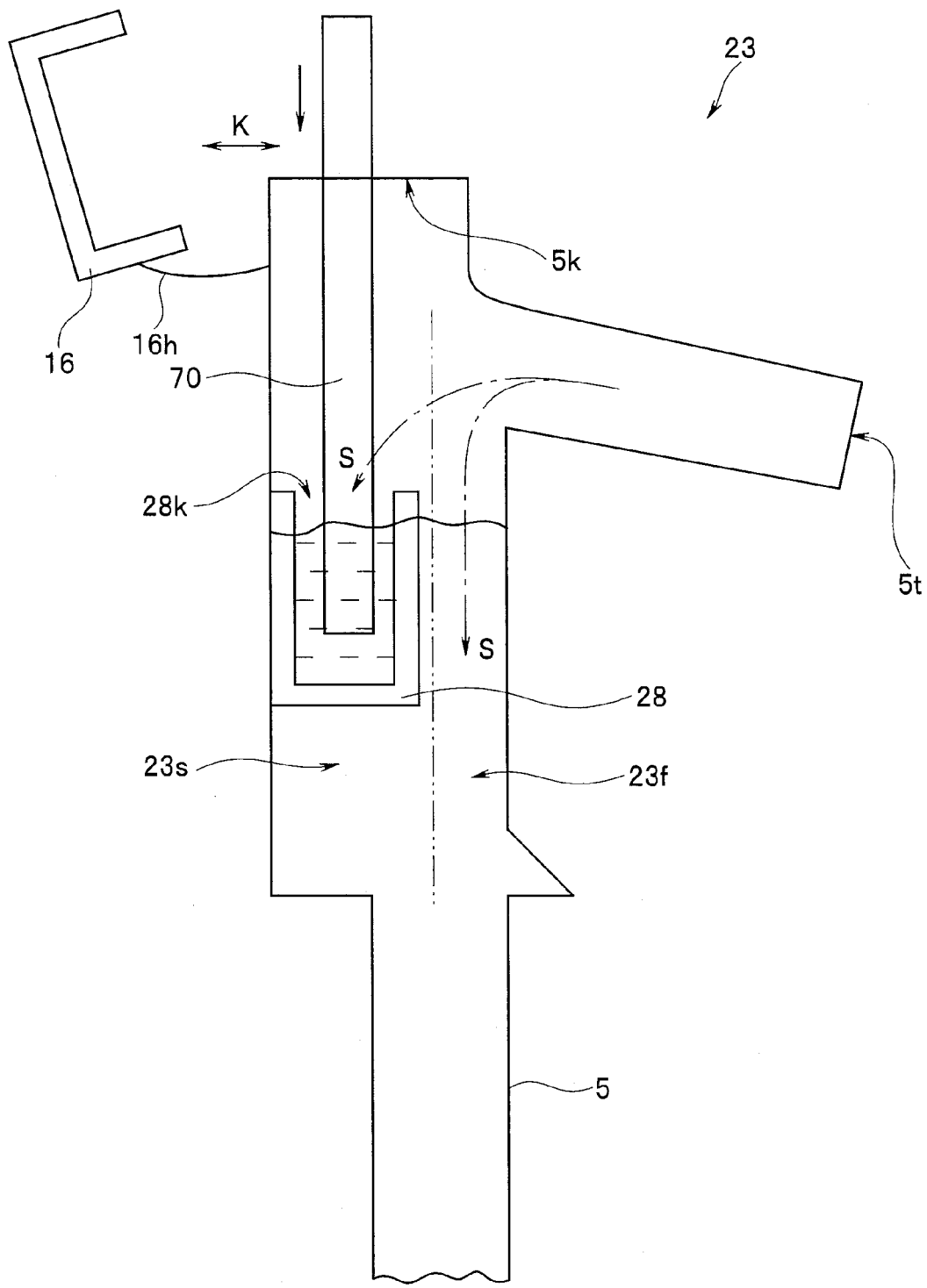
FIG. 7 illustrates a modified example in which a medicinal solution receiving member is configured by a container.

Note that modified examples are described below with reference to FIGS. 7 and 8. FIG. 7 illustrates a modified example in which the medicinal solution receiving member is configured by a container, and FIG. 8 illustrates a modified example of the container serving as the medicinal solution receiving member which is insertable into and extractable from the medicinal solution collecting port.

In the above-described present embodiment, the medicinal solution receiving member is configured by a valve portion such as a check valve, or an electromagnetic valve, however, not limited thereto. The medicinal solution receiving member may be a container 28 which is provided in the second flow passage 23$s$ and which has an opening 28$k$ opening toward the medicinal solution collecting port 5$k$, as shown in FIG. 7.

Figure 8:
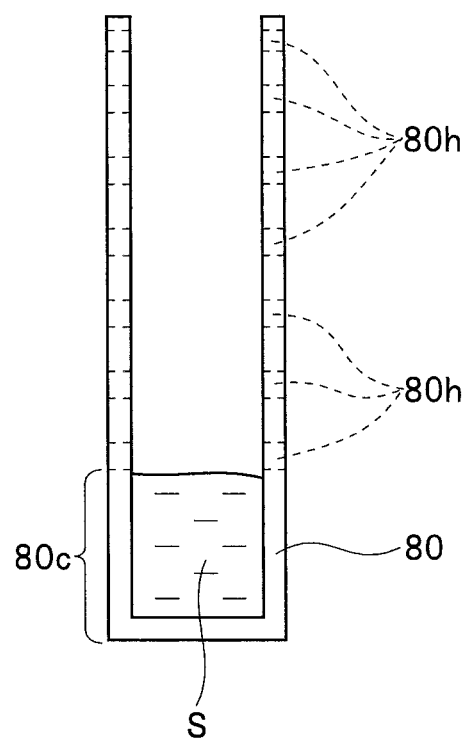
FIG. 8 illustrates a modified example of the container serving as the medicinal solution receiving member which is insertable to and extractable from the medicinal solution collecting port.

In addition, as shown in FIG. 8, the container may be a container 80 which is insertable/extractable through the medicinal solution collecting port 5$k$ and which includes at a lower portion thereof a storage portion 80$c$ capable of storing a predetermined amount of medicinal solution S, and includes a plurality of hole portions 80$h$ at the region other than the region where the storage portion 80$c$ is provided.

If such a container 80 as shown in FIG. 8 is used, the medicinal solution S can be easily collected only by extracting the container 80 out through the medicinal solution collecting port 5$k$, without using the collecting instrument. In addition, even if the worker drops the test paper 70 in the medicinal solution supplying nozzle 23, the dropped test paper 70 is stored in the container 80, thereby enabling the worker to easily take out the test paper 70 only by extracting the container 80 out from the medicinal solution collecting port 5k.

Figure 9:
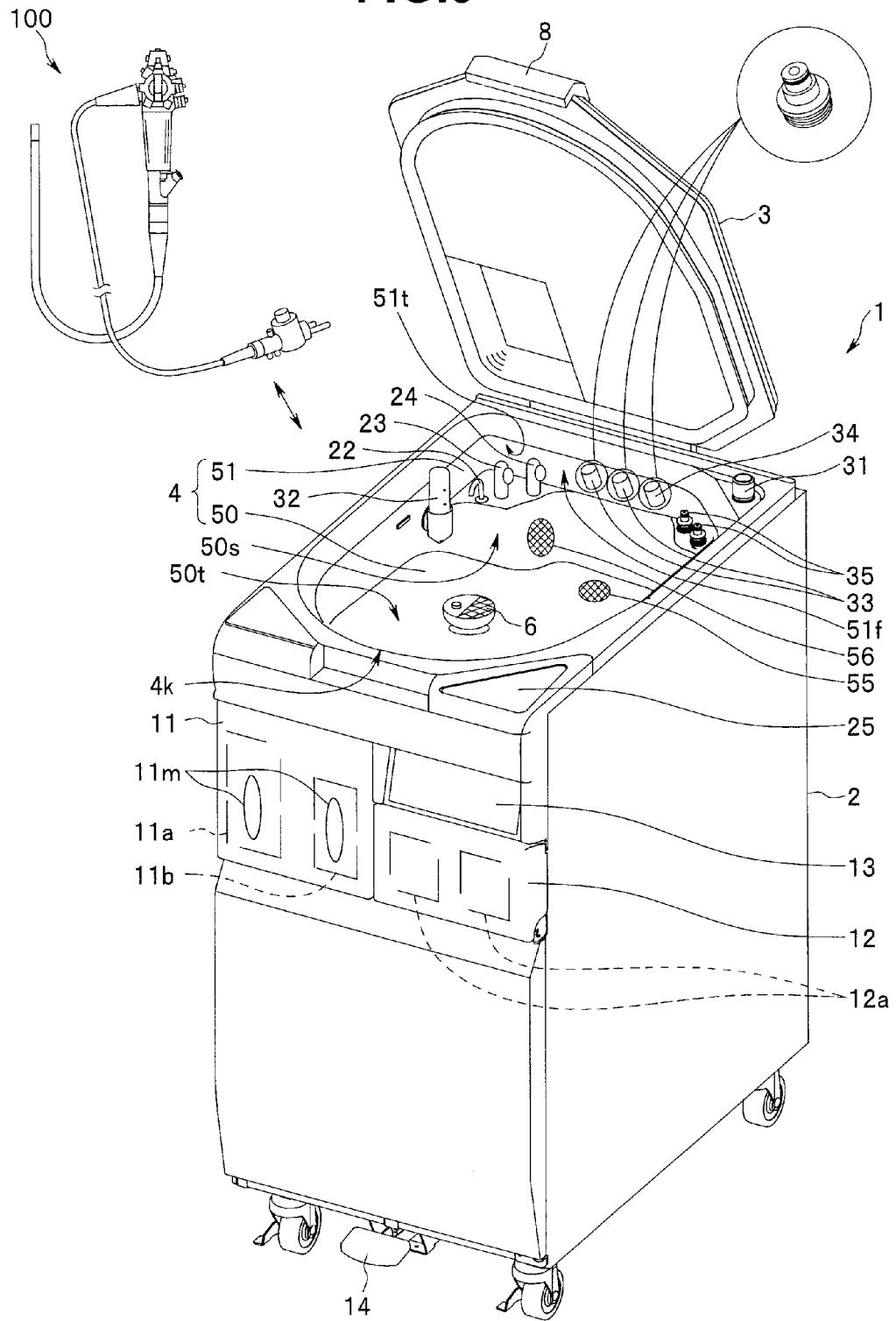
FIG. 9 is a perspective view of the endoscope cleaning/disinfecting apparatus, which shows an example of the endoscope cleaning/disinfecting apparatus in a state where the top cover is open and the endoscope can be housed in the cleaning/disinfecting tank.

Next, one example of the endoscope cleaning/disinfecting apparatus 1 according to the present embodiment will be described with reference to FIG. 9. FIG. 9 is a perspective view of the endoscope cleaning/disinfecting apparatus, which shows an example of the endoscope cleaning/disinfecting apparatus in a state where the top cover is open and the endoscope can be housed in the cleaning/disinfecting tank.

As shown in FIG. 9, the endoscope cleaning/disinfecting apparatus 1 is an apparatus for cleaning and disinfecting the used endoscope 100, and a main part of the apparatus is configured by an apparatus main body 2 and a top cover 3 connected to the upper portion of the apparatus main body so as to be openable/closable through a hinge, not shown, for example.

In a state where the top cover 3 is closed on the apparatus main body 2, the apparatus main body 2 and the top cover 3 are fixed to each other with latches 8, for example, which are respectively disposed at opposing positions of the apparatus main body 2 and the top cover 3.

A cleaning solution/alcohol tray 11 is disposed at an upper part of a left half portion, for example, on the front face, in the drawing, of the apparatus main body 2 so as to be drawable forward of the apparatus main body 2, the front face being a side toward which the operator of the apparatus approaches.

The cleaning solution/alcohol tray 11 houses a cleaning solution tank 11a which is configured to store a cleaning solution as a liquid used for cleaning the endoscope 100 and an alcohol tank 11b configured to store alcohol as a liquid used for drying the endoscope 100 after cleaning and disinfecting. The cleaning solution/alcohol tray 11 is drawable, which enables the respective tanks 11a, 11b to be filled with the liquids appropriately.

Note that the cleaning solution/alcohol tray 11 is provided with two window portions 11m, and the operator can check the remaining amounts of the cleaning solution and alcohol injected in the tanks 11a, 11b from the window portions 11m.

In addition, a cassette tray 12 is disposed at an upper part of a right half portion, for example, on the front face of the apparatus main body 2 so as to be drawable forward of the apparatus main body 2. The cassette tray 12 houses a medicinal solution bottle 12a into which a disinfectant solution such as peracetic acid used for disinfecting the endoscope 100 is injected. The cassette tray 12 is drawable, which enables the medicinal solution bottle 12a to be appropriately set.

Furthermore, a sub operation panel 13 including instruction buttons for displaying cleaning/disinfecting time and warming the disinfectant solution is disposed at the upper part of the cassette tray 12 on the front face of the apparatus main body 2.

Furthermore, at the lower part on the front face, in the drawing, of the apparatus main body 2, a pedal switch 14 for opening upward the top cover 3 closed on the top portion of the apparatus main body 2 by stepping-on operation by the operator is disposed.

In addition, as shown in FIG. 9, main operation panels 25 including setting switches such as a switch for starting cleaning and disinfecting operation of the apparatus main body 2 and a cleaning/disinfecting mode selection switch are disposed on the top face of the apparatus main body 2 at positions near to both ends on the side closer to the front face toward which the operator approaches, for example.

In addition, a water supply hose connecting port 31 is disposed on the top face of the apparatus main body 2 so as to be located closer to a rear face opposing to the front face toward which the operator approaches, the water supply hose connecting port being connected with a water supply hose, not shown, which is connected to a faucet for supplying tap water to the apparatus main body 2. Note that the water supply hose connecting port 31 may be provided with a mesh filter for filtering the tap water.

Furthermore, the cleaning/disinfecting tank 4 which can house the endoscope 100 and has an endoscope housing opening configured to be opened and closed by the top cover 3 is disposed at a substantially center portion on the top face of the apparatus main body 2. The cleaning/disinfecting tank 4 includes a tank main body 50 and a terrace portion 51 provided peripherally so as to be continuous with an outer periphery of the endoscope housing opening of the tank main body 50.

When the endoscope 100 after use is cleaned and disinfected, the tank main body 50 can house the endoscope 100. The tank main body 50 includes, on a bottom surface 50t which is a surface in the tank, a first discharge port 55 for discharging from the tank main body 50 the cleaning solution, the water, the alcohol, the disinfectant solution, or the like which are supplied to the tank main body 50.

Furthermore, at an arbitrary position on the circumferential side surface 50s which is a surface in the tank of the tank main body 50, a circulation port 56 for supplying the cleaning solution, the water, the disinfectant solution or the like supplied to the tank main body 50 to each conduit included inside the endoscope 100, or for resupplying the above-described liquids from a water supply circulation nozzle 24 to be described later to the tank main body 50 through a mesh filter or the like. Note that the circulation port may be provided with a mesh filter for filtering the cleaning solution and the like.

Note that the above-described circulation port 56 may be provided on the bottom surface 50t of the tank main body 50. If the circulation port 56 is provided on the bottom surface 50t of the tank main body 50, it is possible to hasten the timing of supplying the cleaning solution, the water, the disinfectant solution, or the like to each conduit of the endoscope 100 or the timing of resupplying the liquids to the tank main body 50. Furthermore, if the circulation port 56 is provided on the bottom surface, such a configuration provides an advantage for the operator to approach the circulation port, when the user exchanges the mesh filter or the like provided to the circulation port 56.

A cleaning case 6 is disposed at substantially the center portion of the bottom surface 50t of the tank main body 50 of the cleaning/disinfecting tank 4. In the cleaning case 6, buttons such as scope switches of the endoscope 100 and detachable components attached to the endoscope 100 are housed. As a result, the buttons and the detached components are cleaned and disinfected together with the endoscope 100.

At an arbitrary position on the side surface 50s of the tank main body 50, a water level sensor 32 with a cover for detecting a water level of the cleaning solution, the water, the disinfectant solution, or the like supplied to the tank main body 50.

A cleaning solution nozzle 22 for supplying the cleaning solution diluted to a predetermined concentration with tap water from the cleaning solution tank 11a to the tank main body 50 and a medicinal solution supply nozzle (disinfectant solution nozzle) 23 for supplying the disinfectant solution as one example of the medicinal solution S from the medicinal solution storage portion 15 (see FIG. 1) by the medicinal solution supplying member 7 (see FIG. 1) are disposed on a surface of the terrace portion 51 other than a terrace surface 51t, that is, a surface parallel to the bottom surface 50t of the tank main body 50.

In addition, the water supply circulation nozzle 24 for supplying water to the tank main body 50 or resupplying the cleaning solution, the water, the disinfectant solution or the like sucked from the circulation portion 56 of the tank main body 50 to the tank main body 50 is disposed on the surface of the terrace portion 51 which is parallel to the bottom surface 50*t* of the tank main body 50.

Note that the cleaning solution nozzle 22, the disinfectant solution nozzle 23, and the water supply circulation nozzle 24 may be disposed on the terrace surface 51*t*.

A plurality of, for example, two air/water supply and forceps ports 33, for supplying cleaning solution, water, alcohol, disinfectant solution, air or the like to the conduits inside the endoscope 100, a forceps raising port 34 and a water leakage detection port 35 are provided on a surface 51*f* of the terrace surface 51*t* of the terrace portion 51, the surface 51*f* being on a side opposed to an operator approaching position 4*k*.

What is claimed is:

1. An endoscope cleaning/disinfecting apparatus comprising:
    a medicinal solution storage portion configured to store a medicinal solution;
    a cleaning/disinfecting tank in which an endoscope is cleaned and disinfected, the cleaning/disinfecting tank being arranged at a higher position than the medicinal solution storage portion;
    a medicinal solution supplying conduit configured to allow the medicinal solution to pass from the medicinal solution storage portion to the cleaning/disinfecting tank, the medicinal solution supplying conduit having one end communicating with the medicinal solution storage portion and the other end opening toward the cleaning/disinfecting tank;
    a medicinal solution supplying member configured to be driven so as to feed the medicinal solution in a gravity-defying flow direction from the medicinal solution storage portion to the cleaning/disinfecting tank through the medicinal solution supplying conduit;
    a medicinal solution receiving member provided inside the medicinal solution supplying conduit and arranged such that a part of the medicinal solution supplying conduit is located on an upper side of the medicinal solution receiving member in a gravity direction, the medicinal solution receiving member and the part of the medicinal solution supplying conduit forming a medicinal solution remaining portion; and
    a medicinal solution collecting port configured to be openable/closable by a lid body, and provided at a position between the medicinal solution remaining portion and the opening of the other end in the medicinal solution supplying conduit, the medicinal solution collecting port being a separate opening from the opening of the other end in the medicinal solution supplying conduit, wherein
    the medicinal solution receiving member is a check valve configured to allow the medicinal solution flowing from the medicinal solution storage portion to the cleaning/disinfecting tank to pass and configured to receive a part of the medicinal solution fed from the medicinal solution storage portion to the cleaning/disinfecting tank, the part of the medicinal solution being fallen down by gravity without being supplied from the opening of the other end to the cleaning/disinfecting tank due to a stop of driving of the medicinal solution supplying member.

2. The endoscope cleaning/disinfecting apparatus according to claim 1, wherein
    at least a part of other end side including the opening of the other end of the medicinal solution supplying conduit is arranged at a higher position than the cleaning/disinfecting tank, and the other end side is formed to be partly bent such that the other end is open toward the cleaning/disinfecting tank, and
    the medicinal solution collecting port is formed at a top portion on the other end side of the medicinal solution supplying conduit, the top portion being arranged at a higher position than the opening of the other end.

3. The endoscope cleaning/disinfecting apparatus according to claim 2, wherein the medicinal solution collecting port is positioned eccentrically toward a side further away from the other end in a diameter direction of the medicinal solution supplying conduit than a conduit center of the medicinal solution supplying conduit in a region from the medicinal solution collecting port to the medicinal solution receiving member in the medicinal solution supplying conduit.

4. The endoscope cleaning/disinfecting apparatus according to claim 3, wherein the region from the medicinal solution collecting port to the medicinal solution receiving member in the medicinal solution supplying conduit has a linear shape.

5. The endoscope cleaning/disinfecting apparatus according to claim 2, wherein
    the medicinal solution supplying conduit includes, in a region from the medicinal solution collecting port to the medicinal solution receiving member, a first flow passage configured to allow the medicinal solution to pass from the one end to the other end of the medicinal solution supplying conduit and a second flow passage configured to communicate with the first flow passage and linearly connect the medicinal solution collecting port and the medicinal solution receiving member, and
    the medicinal solution received by the medicinal solution receiving member is stored at least in the second flow passage.

6. The endoscope cleaning/disinfecting apparatus according to claim 2, wherein the medicinal solution supplying conduit has, on an exterior portion of a region from the medicinal solution collecting port to the medicinal solution receiving member of the medicinal solution supplying conduit, an indicator for notifying a liquid surface level of the medicinal solution stored by the medicinal solution receiving member.

* * * * *